(12) United States Patent
Lewis et al.

(10) Patent No.: US 8,998,999 B2
(45) Date of Patent: Apr. 7, 2015

(54) HAMMERTOE IMPLANT (71) Applicants: Derek S. Lewis, Copley, OH (US); Amanda M. Martin, Norton, OH (US); James P. Price, Stow, OH (US); Michael A. Zwolinski, Parma Heights, OH (US); David B. Kay, Akron, OH (US)

(72) Inventors: Derek S. Lewis, Copley, OH (US); Amanda M. Martin, Norton, OH (US); James P. Price, Stow, OH (US); Michael A. Zwolinski, Parma Heights, OH (US); David B. Kay, Akron, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 15 days.

(21) Appl. No.: 13/678,005

(22) Filed: Nov. 15, 2012

(65) Prior Publication Data
US 2013/0131822 A1 May 23, 2013

Related U.S. Application Data

(60) Provisional application No. 61/561,049, filed on Nov. 17, 2011.

(51) Int. Cl.
| | |
|---|---|
| A61F 2/36 | (2006.01) |
| A61F 2/46 | (2006.01) |
| A61F 2/42 | (2006.01) |
| A61B 17/68 | (2006.01) |
| A61B 17/72 | (2006.01) |
| A61B 17/86 | (2006.01) |
| A61B 17/88 | (2006.01) |
| A61B 17/84 | (2006.01) |

(52) U.S. Cl.
CPC ............ *A61F 2/4606* (2013.01); *A61F 2/4225* (2013.01); *A61B 17/68* (2013.01); *A61B 17/7291* (2013.01); *A61B 17/864* (2013.01); *A61F 2002/4228* (2013.01); *A61B 17/7258* (2013.01); *A61B 17/8625* (2013.01); *A61B 17/8872* (2013.01); *A61B 17/8897* (2013.01); *A61B 17/848* (2013.01)

(58) Field of Classification Search
USPC .................. 623/21.19, 16.11, 21.15; 606/73, 606/300–304, 309
See application file for complete search history.

(56) References Cited

U.S. PATENT DOCUMENTS

| | | | |
|---|---|---|---|
| 4,940,467 | A | 7/1990 | Tronzo |
| 5,019,079 | A | 5/1991 | Ross |
| 5,029,753 | A | 7/1991 | Hipon et al. |
| 5,062,851 | A | 11/1991 | Branemark |
| 5,360,450 | A | 11/1994 | Giannini |

(Continued)

FOREIGN PATENT DOCUMENTS

| | | |
|---|---|---|
| CN | 201085677 Y | 7/2007 |
| EP | 0880950 A1 | 12/1998 |

*Primary Examiner* — Thomas J Sweet
*Assistant Examiner* — Matthew Schall
(74) *Attorney, Agent, or Firm* — Hudak, Shunk & Farine Co. LPA (57) ABSTRACT

The invention comprises an implant having a first end section and a second end section, where the first end has a cancellous thread for implantation in a first section of bone and the second end includes expansion slots and barbs or wings, that that resist movement out of a second section of bone. These anchors expand outwardly when a rigid wire, such as a k-wire is fed through a central cannulation in the implant and either the wire expands in diameter or the cannulation decreases in diameter. The implant also includes a collar intermediate to the first and second section which includes one or more surfaces to allow the first section to be screwed into a first bone section.

13 Claims, 10 Drawing Sheets

(56) References Cited

U.S. PATENT DOCUMENTS

| | | | |
|---|---|---|---|
| 5,380,334 A | 1/1995 | Torrie et al. | |
| 5,840,078 A | 11/1998 | Yerys | |
| 6,187,009 B1 | 2/2001 | Herzog et al. | |
| 6,451,057 B1 | 9/2002 | Chen et al. | |
| 6,458,134 B1 * | 10/2002 | Songer et al. | 606/304 |
| 7,041,106 B1 | 5/2006 | Carver et al. | |
| 7,780,701 B1 | 8/2010 | Meridew et al. | |
| 7,976,565 B1 | 7/2011 | Meridew | |
| 2002/0183846 A1 | 12/2002 | Kuslich et al. | |
| 2007/0198018 A1 | 8/2007 | Biedermann et al. | |
| 2009/0210016 A1 * | 8/2009 | Champagne | 606/309 |
| 2011/0004255 A1 | 1/2011 | Weiner et al. | |
| 2011/0082508 A1 | 4/2011 | Reed | |
| 2011/0144644 A1 | 6/2011 | Prandi et al. | |
| 2011/0301652 A1 | 12/2011 | Reed et al. | |
| 2011/0301653 A1 | 12/2011 | Reed et al. | |
| 2012/0065692 A1 | 3/2012 | Champagne et al. | |
| 2012/0209337 A1 | 8/2012 | Weinstein | |

* cited by examiner

HAMMERTOE IMPLANT

FIELD OF THE INVENTION

This invention relates to a generally cylindrical intramedullary implant, that is threaded at one end and barbed at the other, for use in joining a bone to another object, including another bone, such as an opposing phalange in a hammertoe procedure. It can also be used for corrections of imbalances in the fingers, and for dental implants. It relates as well to a method of performing procedures for the correction of hammertoe or for trigger finger wherein the implant is threaded into a first phalange and anchored in an adjacent phalange using a guide wire, which activates a mechanism to deploy the barbs into the surrounding bone.

BACKGROUND OF THE INVENTION

The present invention relates generally to orthopedic implants for use in a joint fusion (including fibrous union or even non-union), or as a post for use in a dental procedure. In particular, the implant of the present invention relates to an interphalangeal fusion implant which provides for a stable relationship between two phalanges, such as the proximal phalange and the intermediate phalange, which exists at the proximal interphalangeal joint. Specifically, this implant provides enhanced fixation strength for PIPJ fusion by providing a large cancellous screw thread in the middle phalanx and a longer barbed segment in the proximal phalanx.

Digital deformities of the fingers and toes are some of the most common conditions encountered by small bone specialists. Patients with digital deformities often experience significant pain from structural abnormalitis. Some of these abnormalities are acquired, caused by traumatic injuries, neuromuscular pathologies, systemic diseases, or mechanical problems secondary to extrinsic pressures. Examples of such deformities are popularly known as mallet finger, jersey finger, coach's finger, hammertoe, mallet toe, and claw toe, as well as a host of others, indicative of several different pathologies.

A particular condition, which is suitable for correction using the implant of the present invention, is hammertoe, and related muscular imbalances of the toes. Hammertoes are a contracture of the toes, which result from a muscle imbalance between the tendons on the top and the tendons on the bottom of the toe. Frequently, hammertoes are accompanied by painful corns and callouses. Hammertoe is generally described in the medical literature as an acquired disorder, typically characterized by hyperextension of the metatarsophalangeal joint (MTPJ), hyperflexion of the proximal interphalangeal joint (PIPJ), and hyperextension of the distal interphalangeal joint (DIPJ). In some cases, surgical intervention is the best chance for successfully realigning the toe and for alleviating the pain that accompanies the disorder.

In order to prevent recurrence of the deformity and ensure the success of the surgical procedure, a proximal interphalangeal (PIP) joint arthrodesis is typically performed. The most commonly used hammertoe procedure is that which was described by Post in 1895 and is referred to today as the Post Arthroplasty or Post Procedure. The Post Procedure involves resecting (removing) the knuckle of the toe at the level of the proximal interphalangeal joint (PIPJ). This joint is the joint closest to the point where the toe attaches to the foot. Typically the Post Procedure will be performed in conjunction with a tendon release on the top (extensor surface) of the foot. The combination of these two procedures results in a toe that will lay flatter avoiding direct pressure from the shoe. In the case of a mallet toe or claw toe, the Post procedure may be performed with or without the tendon lengthening. The "end-to-end" or "peg-in-hole" techniques are the most commonly used procedures to resect the PIPJ. The PIPJ is aligned with the rest of the toe in a corrected anatomical position and maintained in place by the use of a 0.045 inch –0.062 inch Kirschner wire (K-wire) driven across the joint. Initially, the wire is placed from the PIPJ through the tip of the toe. It is then driven in retrograde fashion into the proximal phalanx. The exposed wire exiting the toe is bent to an angle greater than 90 degrees, and the bent portion is cut at 1 cm from the bend. At the conclusion of the surgical procedure, a small compressive dressing is placed around the toe, with a Jones compression splint being used for three to four weeks to protect the pin and the toe in order to maintain correction. The K-wire and the Jones splint are generally removed three weeks after surgery.

Similar procedures may be followed to create arthrodesis of the distal interphalangeal joint (DIP) of the toe or for arthrodesis performed in the finger to correct digital abnormalities of the hand. In procedures that involve the use of an implant such as a prior art pin, an incision is made in the top of the toe to expose the affected joint. Subsequently, the surgeon releases the dorsal capsule and extensors tendons at the level of the metatarsal phalangeal joint. Then the extensor tendon is resected and the PIPJ ligaments are released from the medial and lateral sides of the PIPJ. The proximal phalangeal head is resected with a pair of bone nippers, and an implant, such as a pin or a nitinol implant is inserted starting in the proximal bone between the phalanges and the wound is closed.

Although this type of surgical procedure has alleviated the discomfort of hammertoe and other abnormalities of the toe and finger joints for prior patients, there are disadvantages that can surface from the use of the prior art procedures and devices, including swelling, infection at the wound cite, rotation of the affected phalanges, surgical difficulties resulting from overly fussy device material or device, and misalignments resulting from patient non-compliance. In contrast, the present invention assures that the phalanges will remain more securely in the desired relationship for the fusion of the bones, and further creates greater stability at an immediate post-operative stage ensuring greater chances of success regardless of the post-operative compliance of the patient.

The present implant is easier to insert than the prior art implants. It is a single unit integral structure (as used herein "integral" means that it is manufactured out of a material as a single piece, and does not comprise an assembly of components such as two pieces that snap, lock or thread together.) Thus, it does not require the surgeon to assemble components as part of the surgery, but rather allows the surgeon to implant a first end in a first bone segment and to anchor a second bone segment on an opposing second end, for example, in retrograde fashion. It does not require the temperature change that is required in a nitinol implant. Several of the embodiments of the present implant are radially symmetrical or functionally radially symmetrical about the longitudinal axis (i.e., while not radially symmetrical, the placement and sizing of the barbs functions as a radially symmetrical set of barbs would in a cylindrical hole). This eliminates the requirement that the implant is implanted at a specific radial orientation, which may be difficult to achieve or monitor. It also provides more options for the operating surgeon. At his or her discretion, it allows for temporary fixation at the metatarsal, which assists the surgeon by providing a k-wire to guide the implant into the proper position. This feature provides the surgeon with the option of maintaining the wire in the implant to eliminate the common complication of a raised toe from the metatarsal. The pin may subsequently be withdrawn (during that surgery or in a later office visit) without jeopardizing the integrity of the implant if infection due to percutaneous pin is a concern.

SUMMARY OF THE INVENTION

The invention relates to a generally rod-shaped (meaning that there can be flat or uneven longitudinally extending lateral surfaces) or cylindrically shaped implant having a central longitudinal axis extending between a first end and an integral second end. The first end is implanted into a first section (preferably the proximal phalange in the case of a PIPJ fusion) of bone to be joined to another object by means of the unitary (i.e. integral) second end, and preferably to another section of bone, so as to cause the two sections of bone to fuse or be fixed together. Unless otherwise specified, the terms "distal" (meaning outward) and "proximal" (meaning inward) are used with reference to the intended orientation in the body. The first end includes anchoring means, such as for example, cancellous threads that will lodge into the first bone segment. This area of the implant can further include means to drive the first end into the bone, such as an external torque driving shape, for example an external hexagonal collar or flange. Alternatively, the second end can include torque-driving means, for example the longitudinal slots in the sidewalls can be used as driving surfaces or the barbs can include flat up-ward or outward facing surfaces that can be used as driving surfaces.

The second end is constructed as a single piece with the first end and collar and is coaxial with and opposes the first end along the longitudinal axis of the implant. The second end further includes means to secure the second end into a second object, including for example, a dental implant, or a second bone segment, which has been resected for fusion to the first bone segment. This second end includes anchoring means extending radially from a cylindrical base member where the anchoring means, include for example, barbs, ratchets, edges or inverted wings that will allow the implant to be inserted in the second object by a force pushing it in a first direction but which will resist being dislodged from the second object by a force pulling it in a direction opposite to the direction of the first force. Preferably, these anchoring means are provided such that they are radially symmetrical, and including side surfaces, which extend radially and longitudinally and increase (preferably linearly) in diameter in a direction toward the first end. Suitable examples of these barbs include conical collars that have a depth in the direction of the longitudinal axis that is 0.02 to 0.15 mm, and preferably from 0.05 to 0.125 mm long or about 5-30%, and preferably from about 10 to about 20% of the length of the second section from collar edge to tip. Thus, the present invention is distinguished from the use of threads or edges on the second anchoring section. Advantageously, the present invention is cannulated to allow a wire to be used subcutaneously through the tip of the toe, and into the proximal phalanx and metatarsal to retain the straightened toe in a flat position while the fusion occurs (i.e. to avoid the toe bending upward after the procedure.)

An additional and unique optional feature of the present invention is an elegant solution to securely anchoring the second end of the implant in the second bone segment, in particular by including a restriction or a reduction within the cannulation, and by providing for the anchoring means to be radially flexible. For example, the anchoring means can be barbs extending from a generally cylindrical base, where the barbs include side surfaces that define conical sidewalls or portions thereof, where the barbed cannulated end includes one or more radial longitudinal splits that allow the terminal shoulders of the conical portions to flare radially outward when a restricted or reduced area of the cannulation encounters a wire having a diameter of greater diameter than the cannulation in its base configuration and also allow the shoulders to flex radially inward when the wire is not in the restricted area. Thus, preferably, the barbs are formed as larger diameter conical collars having a sidewall that increases in diameter toward the first end of the implant and which terminate at an edge formed at the junction of the conical sidewall and a distal facing surface which joins the collar to the base. The longitudinal splits or slots permit the anchoring area of the sidewall and edge to compress inwardly to allow the second end to be inserted into an undersized pre-drilled hole in the second bone segment (within the cortical shell of the bone), but which will extend radially outwardly in response to a force pulling the implant out from the pre-drilled hole.

It should be understood that radial portions (possessing both a length along the longitudinal axis and a width which is a portion of the circumference for a conical shape or a flattened version of these) of these conical collars may also be used. Where there are multiple levels along the longitudinal axis, they may be radially offset to each other. It can be seen that the invention relates to a surface structure which includes greater surface area than a thread, hook, or edge and that increases in diameter in the distal direction along the longitudinal axis and advantageously includes a sharp edge or shoulder at the distal terminus of the barb so as to allow a stress shielded sliding into the bone. This provides a preferential sliding of the implant in one direction over the other in the hole that has been pre-drilled in the bone section. Alternatively, the second end can comprise inverted wings, shoulders or flanges that have a reverse angle and that flex radially inward so that the second end can be inserted into an undersized pre-drilled hole but which will flex to resist longitudinal movement out of the hole once the implant is in position. It is likewise envisioned that the first end could include such anchoring means in lieu of the threads previously described.

Thus, in a first embodiment, the invention comprises an integral (i.e. made from a single piece and being free from assembly during the surgical procedure and/or before) rod-like implant having along a longitudinal axis, a first end opposing a second end, where the first end has a cancellous thread, the second end including radially extending conical collar forming barbs or shoulders that include an inverted surface so as to resist movement out of a second section of bone. In particular, the inverted surface forms an angle preferably equal to or less than 90° with the longitudinal axis in the direction toward the first end of the implant. The purpose is to define a relationship with the second bone so that the shoulder or shoulders expand and lodge within the second section of bone. Further, the implant includes a cannulation aligned with the longitudinal axis (i.e. is co-axial therewith) as well as means which permit the second section of implant to expand radially, including for example, one or more and more preferably two or more radial expansion slots parallel to the longitudinal axis and coupled with a restriction or reduction in diameter in the central cannulation. Alternative means to cause the expansion could include a weakened wall section that will allow the second section to collapse or crush in the longitudinal direction to form an interference fit with the second bone section. The central cannulation can include multiple restrictions or reductions in diameter or alternatively, the k-wire that is used with the implant can taper or increase in diameter so as to expand the second section of the implant. The second end of the implant can include a single series of barbs (or collars) or a series of stepped barbs (or collars). Advantageously, at least one of the barbs is located distal to (or in the direction of the first end past) the end of the longitudinal slots. Preferably, this embodiment of the implant also includes a collar intermediate to the first and second section, which includes one or more surfaces to allow the first section to be screwed into a first bone section. Advantageously, this collar defines a hexagonal torque-driving surface.

In alternative embodiments of the invention, at least one section includes a set of wings for example which, taper outwardly away from a central opening where the wings will deflect inwardly in the central opening during implantation in the second section of bone but which will resist removal from the bone, and the invention includes a full cannulation along the longitudinal axis.

BRIEF DESCRIPTION OF THE DRAWINGS

FIG. 17(a)-(j) illustrates the method of the present invention for use in a hammertoe procedure.

DETAILED DESCRIPTION OF THE INVENTION

Figure 1:
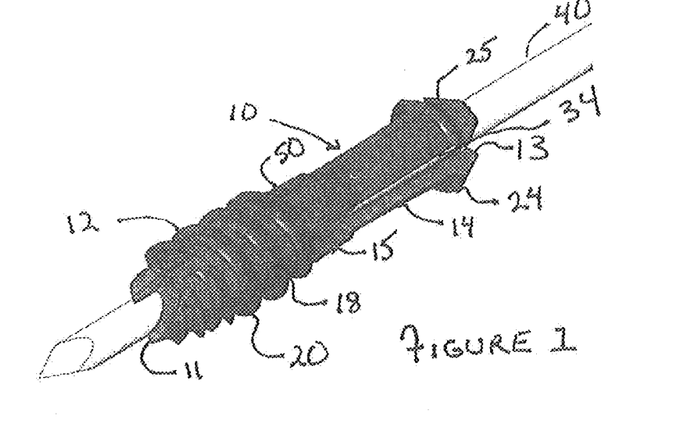
FIG. 1 is a perspective view from the top and the proximal end of the hammertoe implant present invention on a k-wire.
Figure 2:
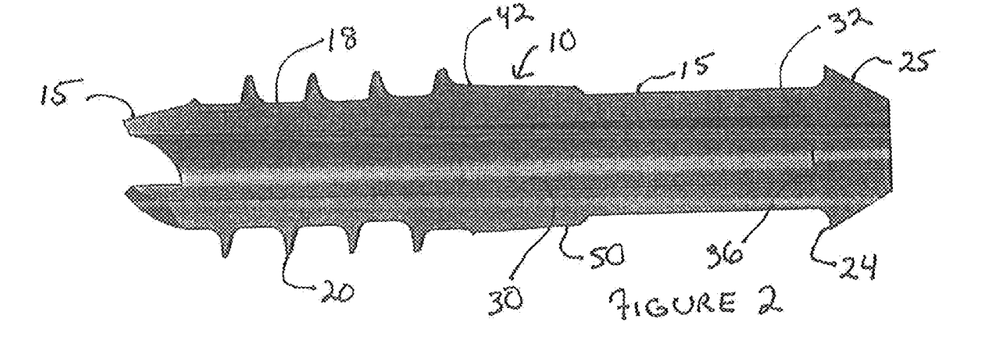
FIG. 2 is a cross section taken along a central longitudinal axis of a implant illustrating a first embodiment of the cannulated implant with a radially expanding mechanism in accordance with the present invention.
Figures 3, 4, 5:
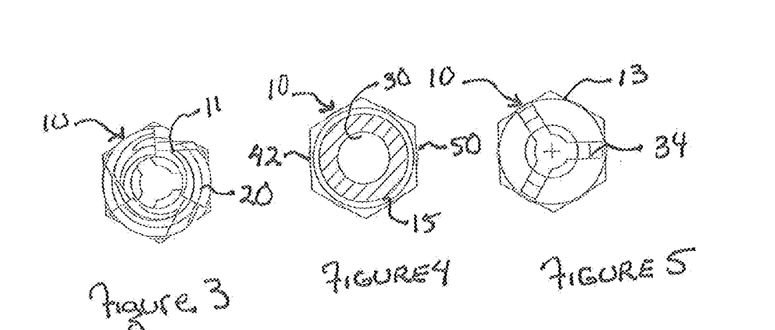
FIG. 3 is a first end view of the hammertoe implant of FIG. 2.
FIG. 4 is a second end view of the hammertoe implant of FIG. 2.
FIG. 5 is a cross section taken along a plane transverse to the longitudinal axis through the intermediate section.

As shown in FIG. 1, the invention comprises an integral rod-shaped implant 10 having along a longitudinal axis, a first end section 12 including a first end 11 and an opposing a second end section 14 including a second end 13. The implant can be provided in various sizes to accommodate different phalanges or size toes. It is envisioned that three sizes may be provided, a small, medium and a large. In all cases, the total length of the implant is from 0.3 to 1 inch, and preferably 0.4 to about 0.7 inch. The first section has a length of about 0.2 to about 0.4 inch, and preferably around 0.3 inch with a major diameter of about 0.165 inch for the larger implant (0.150 for the smallest medium implants) and a minor diameter of about 0.11 inch for the larger implant (0.098 for the small and medium implants). The second end section has a similar length, which is preferably about 0.03-0.05 inch longer. The first end section 12 is shown with a self-drilling section of 1-4 pointed and sharp edge members 15 defined by a tapered, beveled section of minor diameter that extends beyond the thread run out Optionally, the implant can include at least one and preferably 2-5, and more preferably 3 cutting flutes. The first end section 11 also has on its exterior cylindrical minor surface 18, a robust cancellous thread 20 for implantation into the proximal phalange.

Figure 6:
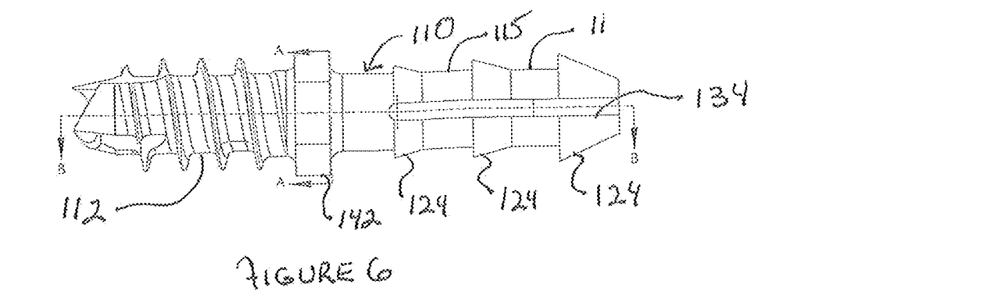
FIG. 6 is a side view of a second embodiment of the hammertoe implant of the present invention.
Figure 7:
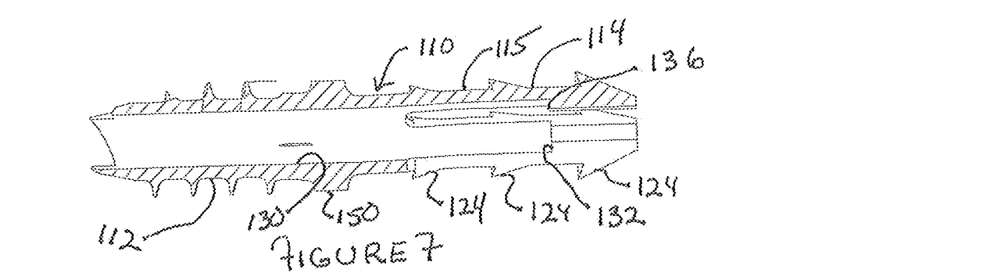
FIG. 7 is a cross-section of the embodiment of the hammertoe implant of FIG. 6 taken along a plane intersection the longitudinal axis.

The second end section of the invention 14 includes anchoring means, and more specifically barbs or ratchets 24 extending away from a cylindrical base 23 having a minor diameter of 0.07 inch, where the barbs can include one or more conical sections 25 joined by a edge to the base to form a sharp edge 26 and the conical sections having a length along the longitudinal axis of from about 0.03 to about 0.08 inch. The conical sections include side extending surfaces which preferably form a radial and/or longitudinal portion of a cone or a geometrical construct that expands radially like a cone but is constructed of flat surfaces. In the embodiment of the invention illustrated in FIGS. 6 and 7, the implant 110 includes a second end section 114 having three barbed sections 124 of increasing size, having a length in a first barb section of 0.07 inch and a diameter of 0.126 inch for the larger implant (a length of 0.05 and a diameter of about 0.08 for the small implant and a length of 0.06 and a diameter of 0.102 inch for the small implant), having a length in a second barb section of 0.055 inch and a diameter of 0.115 inch for the larger implant (0.042 inch in length and a diameter of 0.098 for the small or medium implant) having a length in a third barb section of 0.04 inch and a diameter of 0.108 inch for the larger implant (0.03 inch in length and 0.094 inch for the small or medium implant). The conical surfaces taper in diameter to increase toward the direction of the first end section 12 (or for the second embodiment the corresponding first end section 112). The second end section 12 (112) has a constant or tapered minor diameter (0.07 inch for the small implant and 0.08 for the medium implant) to define shoulders that extend in the radial direction from 0.005 to about 0.018 inch. In addition, these shoulders form an acute angle of from about 45° to about 90°, and preferably about 60° to about 80° to the exterior minor surface 15, (115) of the second section so as to form inverted surfaces 28 that resist movement out of a second section of bone. As used herein the dimensions are recited so as to support the use of the term "of" and "of about" wherein the latter is preferably is interpreted as including +/−20%, and more favorably +/−15% or even 10%. The conical collars are interrupted by 2-5 and preferably 3 longitudinally extending radial slots in the side wall of the base and conical collars and which extend in the direction of the longitudinal axis of the longitudinal axis of the implant. These slots allow the side walls of the second section to form fingers that flex radially inwardly when the conical surfaces of the interrupted collars encounter the pressure of a hole pre-drilled in the second bone section (i.e. that bone section which is fixed to the bone section that houses the first end section of the implant, and more specifically, the intermediate phalange). While the implant is illustrated with full conical collars that are interrupted only by the longitudinal slots, it should be understood that portions of these conical collars can also be used.

Figure 8:
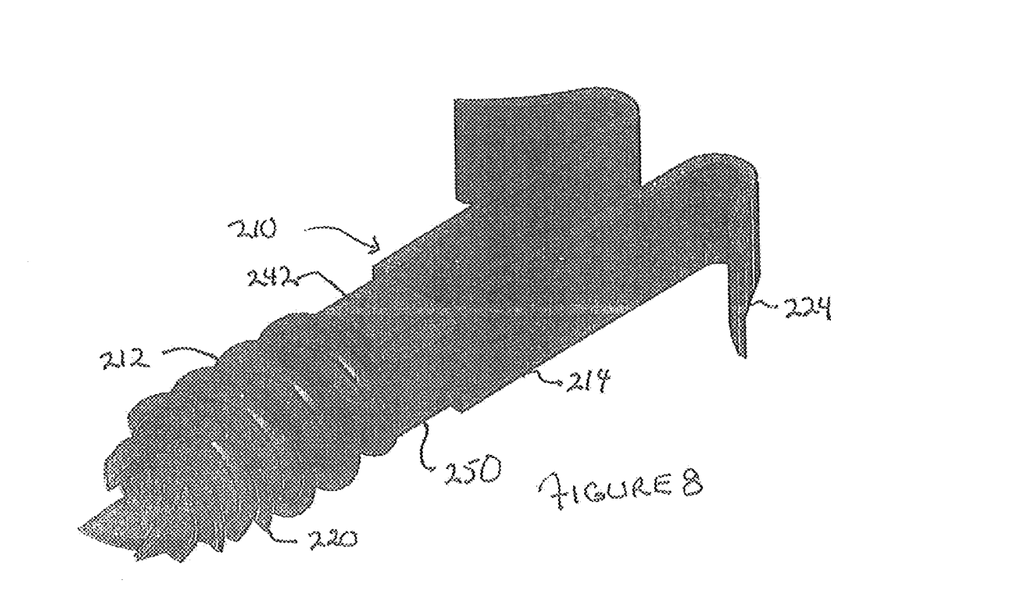
FIG. 8 is a perspective view from the top and the distal end of a third embodiment of the hammertoe implant present invention.

FIG. 8 illustrates a third embodiment of the implant of the invention 210 having a first end section 212 with threads 220 and a second end section 214 with flexible anchoring wings 224 that act to anchor the implant in the smaller pre-drilled hole in the second section of bone. The purpose of the barbed section of the implant is to define a relationship with a second bone segment so that the anchoring members 24 (124,224) expand and lodge within the second section of bone.

Further, the implant 10 (110, 210) optionally includes a cannulation 30 (130) aligned with the longitudinal axis (i.e. co-axial therewith) coupled with expansion means 32 (132) which permit the second end section 14 (114) of implant 10 (110) to expand radially. In the embodiment shown in FIGS. 1-5, for example, the expansion means comprises the conical sections 24 described above and the second end section 14 further has one or more, and preferably two or more radially spaced expansion slots 34 which run parallel to the longitudinal axis for a substantial length of the second section, (i.e., about 0.2 to about 0.3 inch) coupled with a restriction or reduction 36 in the diameter in the central cannulation 30 (i.e. at a depth of about 0.1 inch +/−0.05 from the second end, and of a decrease of about 0.02 inch +/−0.01 for a central cannulation of about 0.66 inch for the larger implant or 0.047" for the small implant for a correspondingly sized K-wire). In the second embodiment the restriction 136 is also formed along the section including the expansion slots 134 in the cannulation 130. Alternative means to cause the expansion could include a weakened wall section that will allow the second section to collapse or crush in the longitudinal direction to form an interference fit with the second bone section. Alternatively, the central cannulation can include multiple restrictions or reductions in diameter or alternatively, the k-wire 40 that is used with the implant can taper or increase in diameter so as to expand the second section of the implant.

Preferably, the first embodiment of the implant 10 (110, 210) also includes a collar 50 (150, 250) having a length of about 0.050+/−0.005 inch intermediate to the first end section 12 and the second end section 14 which includes one or more, (and preferably from about 3 to about 8) radially flat exterior surfaces 42 (142, 242) to allow the first end section to be screwed into a first bone section. Advantageously, this collar defines a hexagonal torque-driving surface. The implant is made from a suitable biocompatible material, for example, such as medical grade stainless, titanium or titanium alloy, nitinol, ceramic or PEEK or similar implantable polymeric material. Optionally, the guide wire may include means to avoid infection, such as an antimicrobial treatment and/or a cap at the wound site.

Figure 13:
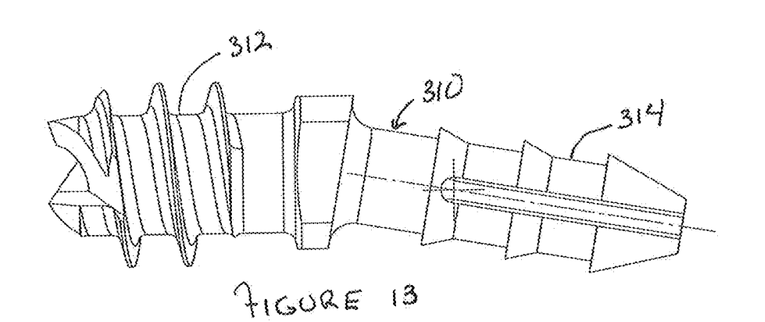
FIG. 13 is a first side view of an alternative embodiment of the hammertoe implant of the present invention.
Figure 14:
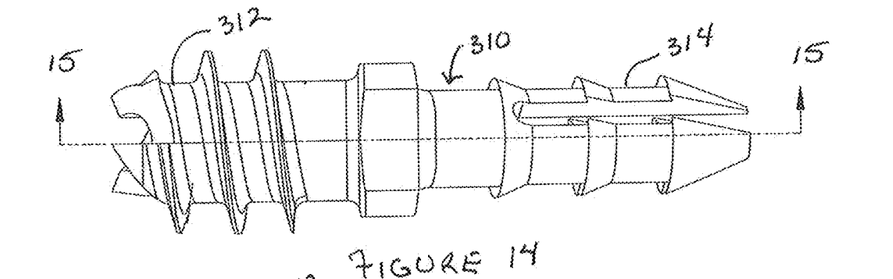
FIG. 14 is a second side view of the hammertoe implant of FIG. 13 taken at 90° to the view of FIG. 13.
Figure 15:
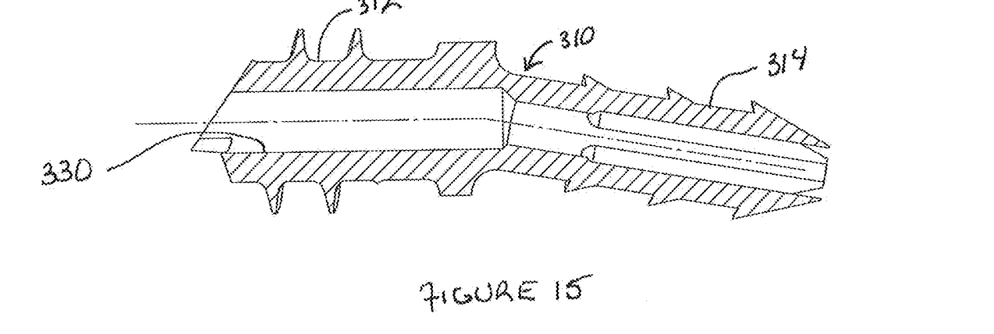
FIG. 15 is a cross section taken along line 15-15 in FIG. 14.

FIGS. 13-15 illustrate a third embodiment of the invention in which the implant 310 includes the threaded first section 312 joined to the barbed second section 314 but in which the second section 314 is angled with respect to the first section 312. This angle is from 5° to 25°, and more preferably is 10°+/−2,° or at angles of 8°, 10° and 12°. This version continues to include the cannulation 330 which is sized to allow a relatively thin guide wire to be threaded through the cannulation. The radial activation mechanism comprising the combination of the radial slots and the restriction in the cannulation is optional in this version, and is not illustrated in the Figures.

Figure 9:
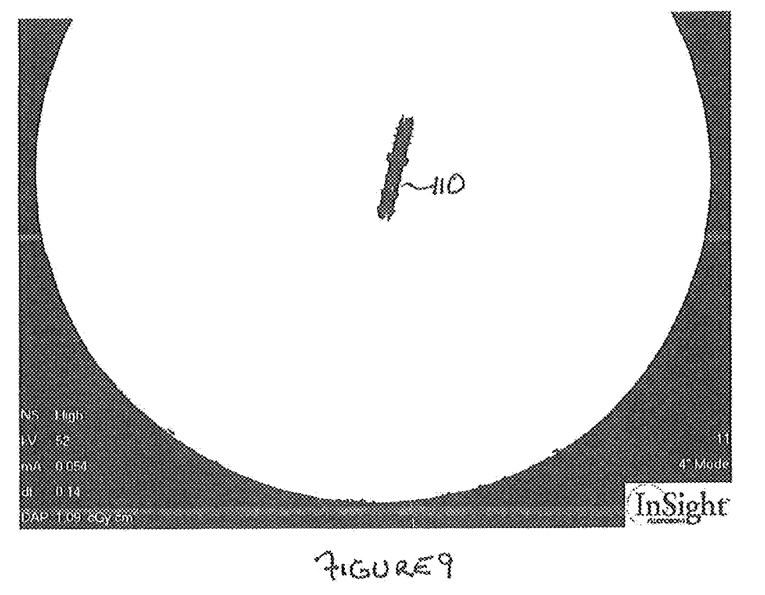
FIG. 9 is the fluoroscopy images of the implant in accordance with the present invention.
Figure 10:
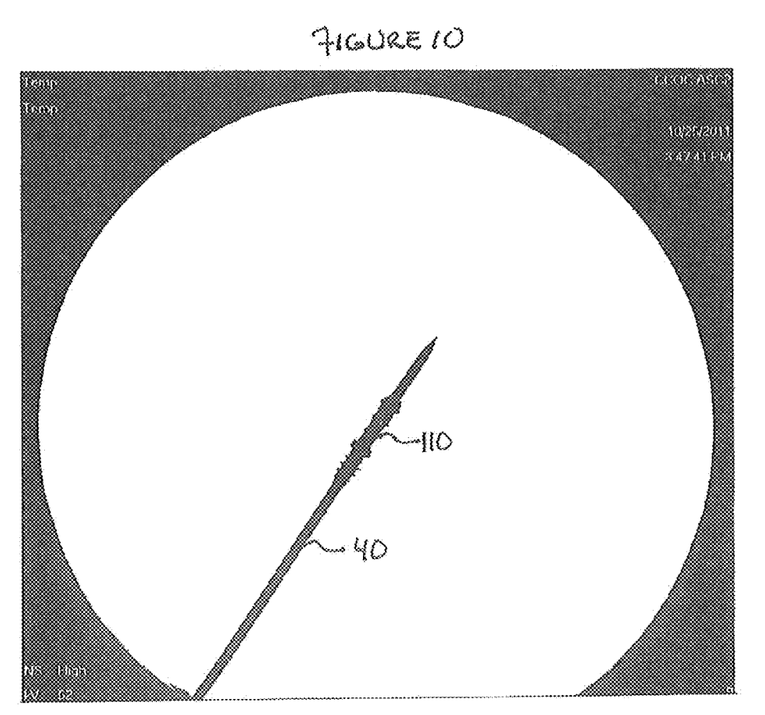
FIG. 10 is a fluoroscopy image of the implant of FIG. 8 on a K-wire.
Figure 11:
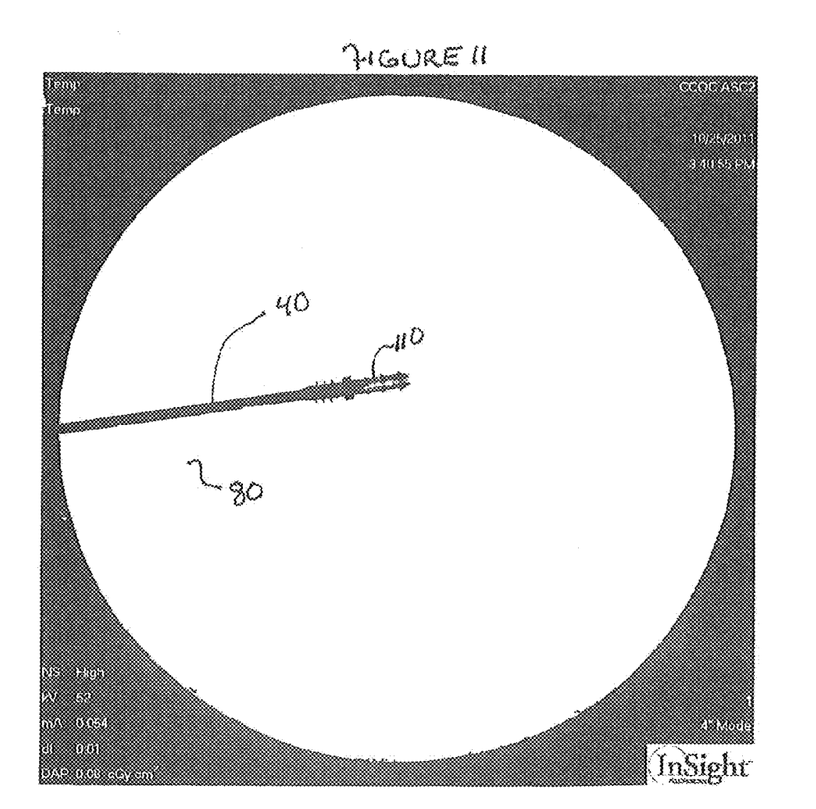
FIG. 11 is a fluoroscopy image of the implant of FIG. 8 on a K-wire; with the first section implanted into a sawbone.
Figure 12:
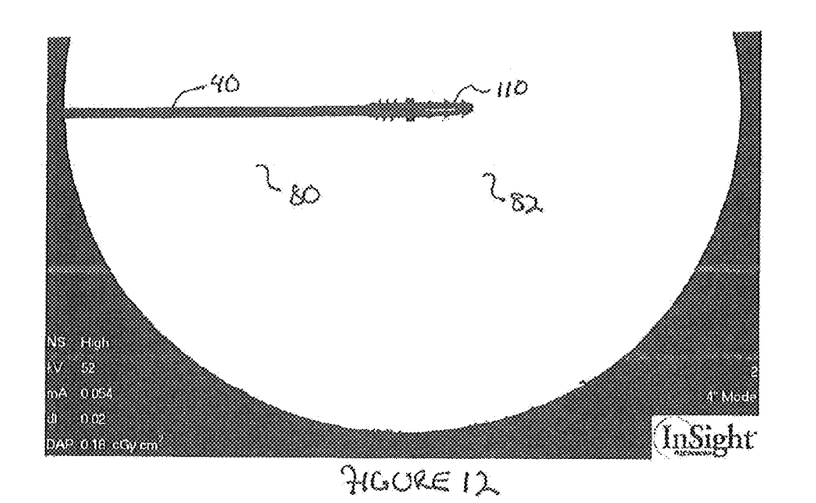
FIG. 12 is a fluoroscopy image of the implant of FIG. 8 on a K-wire with both sections implanted into sawbones.
Figure 16:
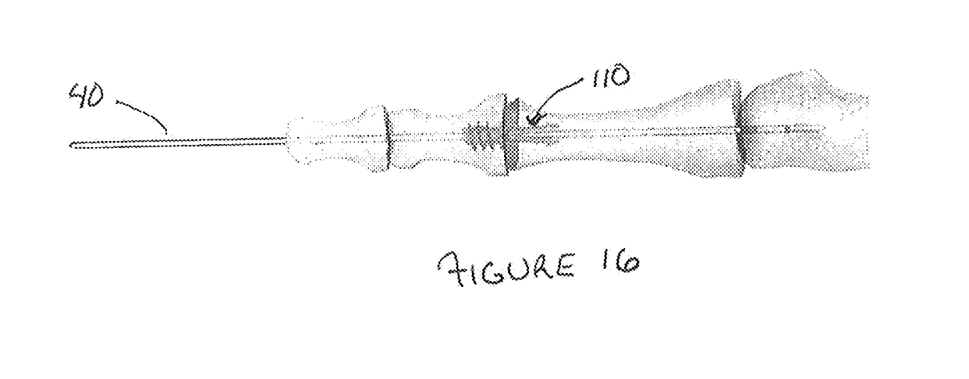
FIG. 16 is an illustration of the present invention used in a PIPJ fusion.

FIGS. 9-12 are fluoroscopy images of the implant in a sawbone. FIG. 9 illustrates the static state of the implant 110 without the wire. FIG. 10 illustrates the implant 110 in the expanded position with the wire 40 inserted past the restriction in the cannulation. FIG. 11 illustrates the first section of the implant 110 threaded into a bone 80 (in this case, a sawbone) and FIG. 12 illustrates the implant 110 in two sections of bone 80, 82 with the wire 40 retracted. FIG. 16 illustrates the implant 110 of the present invention in place in a PIPJ fusion.

Figure 17A:
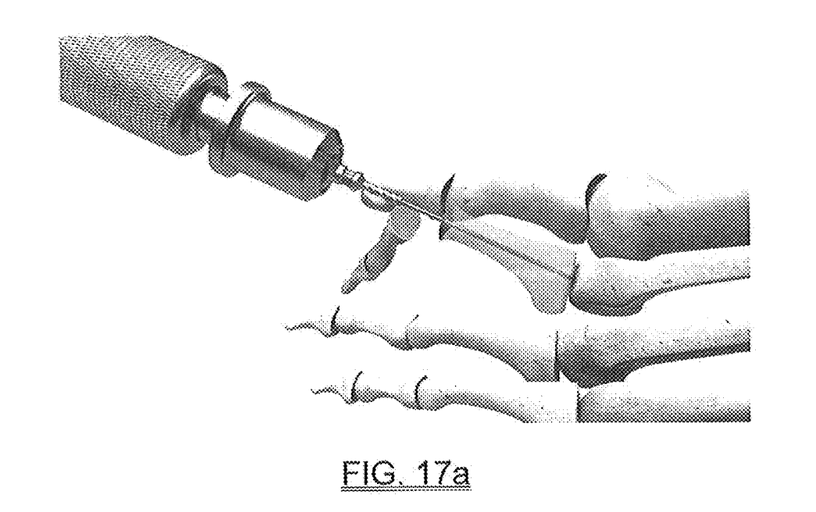

The following operative technique outlines the implantation of the Intraosseous Fixation System implant along with temporary guide wire stabilization of the MTP joint. Various steps are illustrated in FIG. 17(a)-(j). The benefits of utilizing the guide wire are prevention of MTP subluxation and increased initial implant stability.

Step 1: The implant images on the caddy lid are used as a template for the patient's radiographs to select the appropriate size implant. The caddy lid depicts true scale images of the implants in neutral and deployed geometry so that the entire profile of the implant fits within the cortical shell of the operative phalanges and the use of fluoroscopy is recommended against since it may not display image to scale.

Step 2: An incision over the dorsal aspect of the PIP joint is created and a transverse capsulotomy is performed with release of the collateral ligaments off the head of the proximal phalanx. The joint dissection and access should provide complete visualization of the articular surfaces of the middle and proximal phalanges see FIG. 17(a).

Figure 17B:
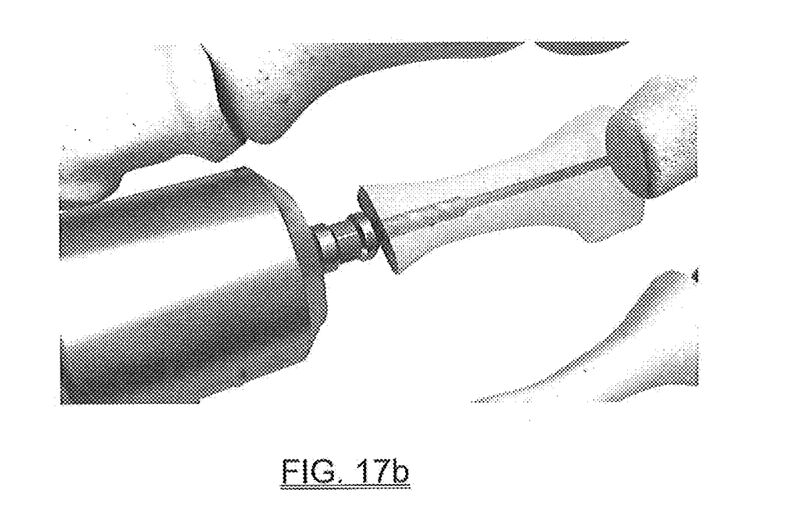

Step 3: Cuts are made perpendicular to the long axis of each phalanx to achieve a straight toe orientation. The distal head of the proximal phalanx just posterior to the head of the phalange is resected and a slight resection is also required of the subchondral bone of the middle phalanx see FIG. 17(b). If the toe is desired to be fused at an angle, it is necessary to prepare the resection of the bones at the appropriate angle and consideration of excision of the plantar plate is recommended.

Step 4: The appropriate implant size is selected (determined from the radiographic template) along with the corresponding guide wire. If implant verification is desired with fluoroscopy, the actual implant over a guide wire is used.

Step 5: The trocar tip of the guide wire is inserted into the proximal phalanx along its central axis and the correct position of the guide wire is verified with dorsal-plantar and medial-lateral fluoroscopy views. After the wire location has been verified, the advancement of the wire is continued until it pierces the proximal cortex of the proximal phalanx. A correct trajectory of the implant is assured to prevent interference with the cortex on implantation and prevent Incorrect juxtaposition and subsequent issues with healing of the fusion site. Preferably the guide wire is started by hand and will naturally find the intramedullary canal.

Step 6: Based on implant selection, the appropriate cannulated drill bit is selected. Color-coded drill bits that correspond with the implant are provided in the system: 1.7 mm (gold), 2.0 mm (green), and 2. 5mm (blue). Drilling is commenced over the guide wire until the depth indicator line on the bit meets the cut surface of the proximal phalanx and the guide wire is removed.

Figure 17C:
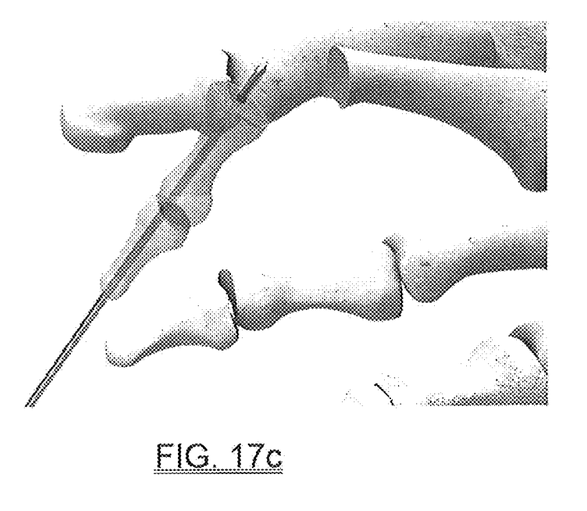

Step 7: The trocar tip of the guide wire is inserted into the middle phalanx along its central axis. The correct position of the guide wire is verified with dorsal-plantar and medial-lateral fluoroscopy views. After the position has been verified, the guide wire is continued to be driven distally by engaging the wire driver's collet on the distal end of the guide wire and pulling) until the laser etched line on the conical tipped end of the wire just contacts the cut surface of the middle phalanx and through both middle and distal phalanges until it exits the toe. See FIG. 17(c).

Step 8 (Optional): If needed, a countersink is provided to ensure the implant drive (i.e. the collar) feature can be buried below the cut surface of the middle phalanx. The countersink is inserted onto the handle provided and the countersink is placed over the exposed wire and rotated several times so that the countersink shoulder bottoms out on the cut surface of the middle phalanx.

Figure 17D:
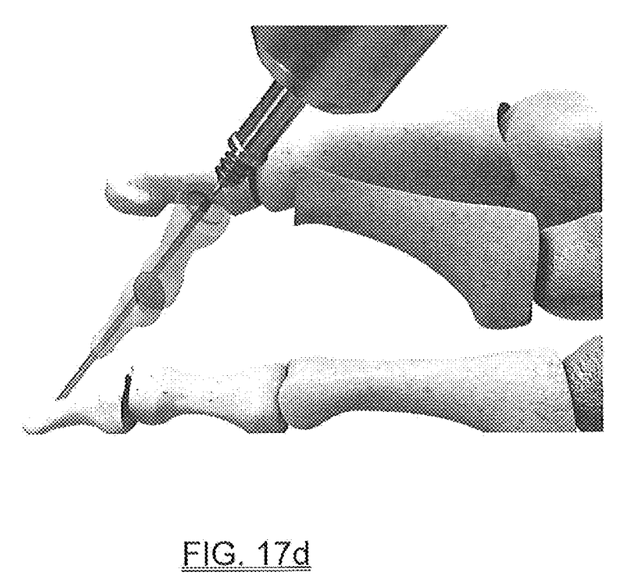
Figure 17E:
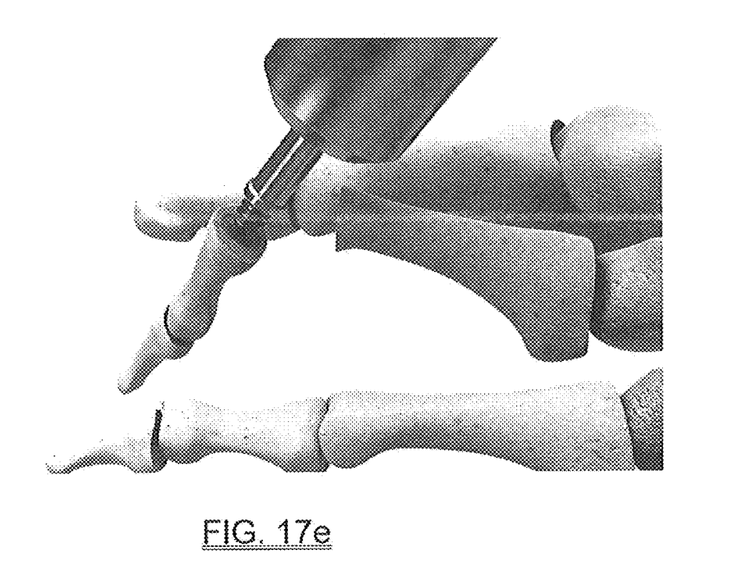
Figure 17F:
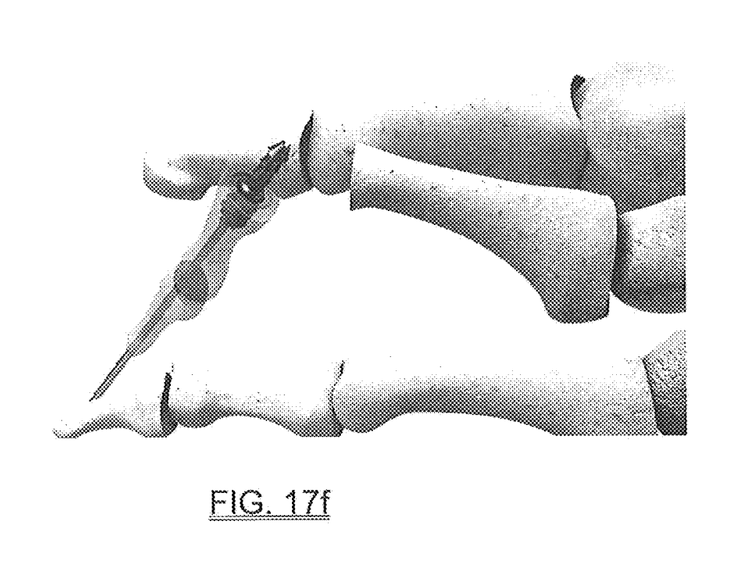

Step 9: An implant that is preloaded onto the driver socket is selected and the socket is attached to the handle. The implant/socket/handle assembly is placed over the guide wire. The threaded portion of the implant is driven into the middle phalanx by screwing it in place. See FIGS. 17(d,e). The threaded portion is driven until the hexagonal drive feature is buried in the middle phalanx and the driver socket is disengaged from the implant. See FIG. 17(f). The driver socket is removed and disposed from the implant leaving the barbed portion exposed.

Figure 17G:
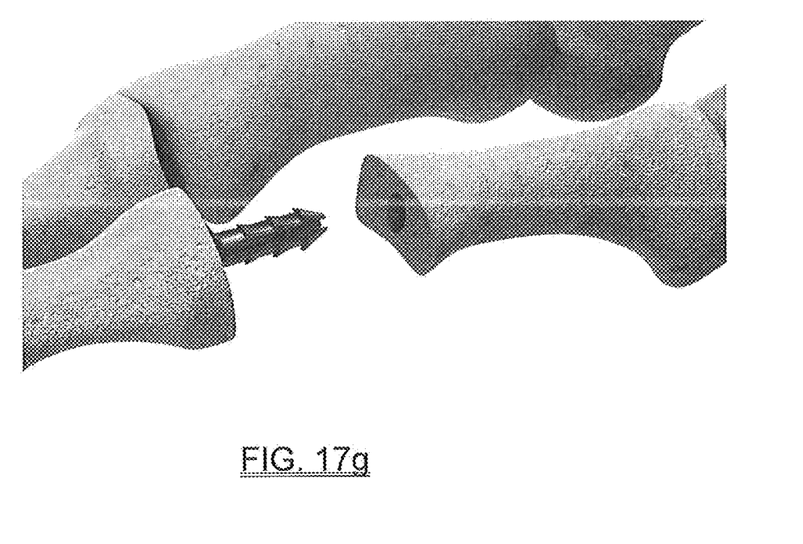

Step 10: The implant is positioned in line with the proximal phalanx and the barbed portion of the implant is inserted into the pre-drilled hole in the proximal phalanx. See FIG. 17(g). An axial force is applied (firmly compressing the joint) until the implant is completely buried and the opposing faces of the middle and proximal phalanges come into contact which is confirmed with fluoroscopy. Any overhanging bone at the fusion site should be excised.

Figure 17H:
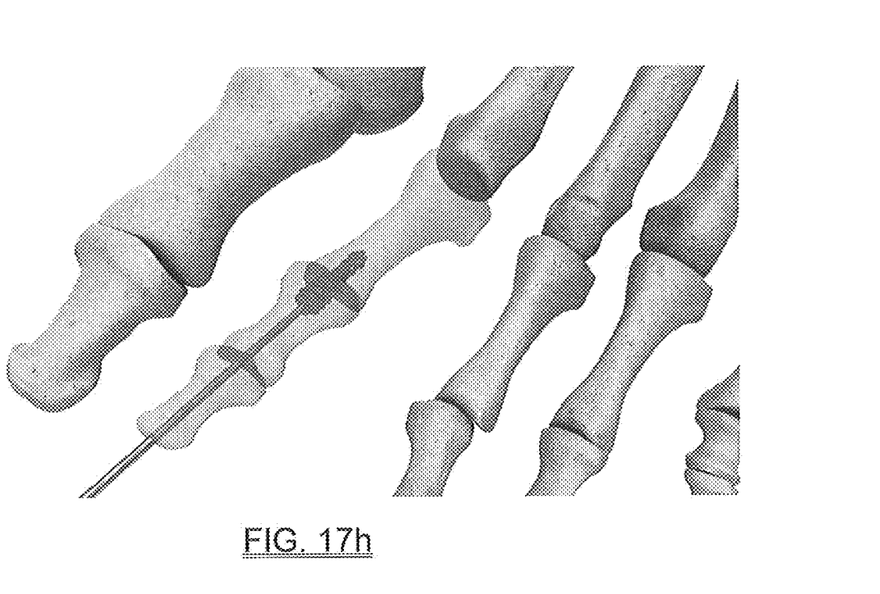
Figure 17I:
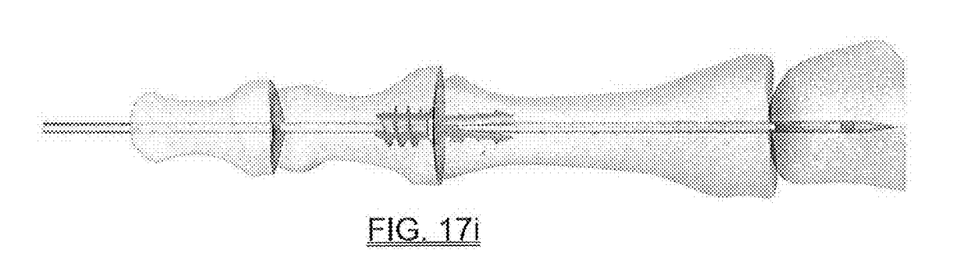
Figure 17J:
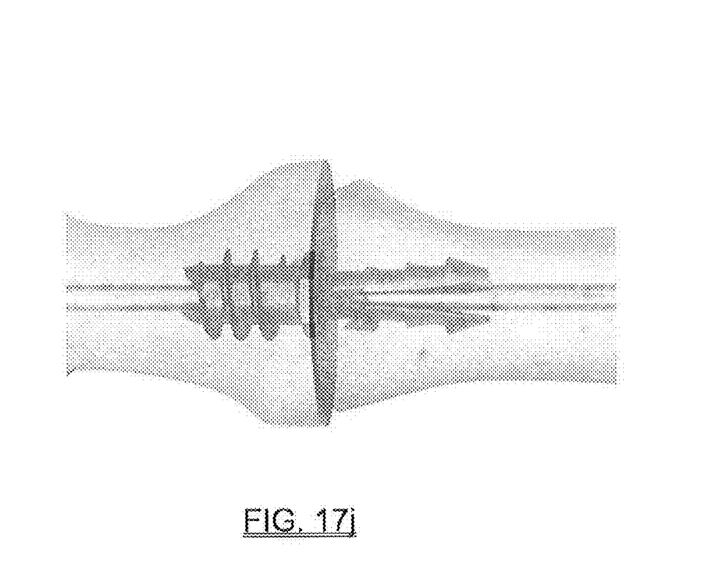

Step 11: The conical tip of the guide wire is driven proximally through the implant and back into the metatarsal to stabilize the MTP joint. See FIGS. 17(h,i). This will cause the barbed portion of the implant to expand and hold into the bone. Based on the surgeon's discretion, the guide wire fixation of the toe to the metatarsal can be left in place for the initial recovery period to allow the soft tissues to heal and prevent MTP joint subluxation. See FIG. 17(j). Optimal fixation strength is obtained by leaving the wire in the implant.

Step 12: The correction and the implant positioning are verified in multiple views using fluoroscopy.

Step 13: The surgical site is closed according to surgical preference. If the guide wire is temporarily left in place, it is trimmed with wire cutters, and the exposed end is covered with a Jurgan ball.

If the implant is intended for placement without the guide wire, it is used for placement of the proximal first end section and removed prior to the retrograde placement of the intermediate phalange on the second end of the implant.

While in accordance with the patent statutes the best mode and preferred embodiment have been set forth, the scope of the invention is not limited thereto, but rather by the scope of the attached claims.

What is claimed is:

1. A fusion implant system comprising a rigid wire having an external diameter and an implant having a first end section including a threaded portion that is capable of being implanted in a first bone section and an integral second end section comprising at least two fingers that apply a radially outward force that is capable of holding an object in relation to the first bone section, where the implant has a central cannulation having a first internal diameter that is sufficiently large to accommodate the diameter of the rigid wire and which extends through the first and second end sections and the implant includes a radial expansion mechanism in which either the cannulation has a reduction in diameter in the second end section from the first diameter to a second diameter which is smaller than the diameter of the rigid wire, or the rigid wire has an increase in external diameter which is greater than the first internal diameter of the central cannulation, and each of the fingers of the second end section has an external surface which includes an anchoring barb member that deflects radially outwardly when radial expansion mechanism is activated.

2. The fusion implant system as set forth in claim 1, wherein the second end section has a cylindrical surface and the radial expansion mechanism comprises one or more longitudinal expansion slots in the cylindrical surface of the second end section so as to form the fingers and the fingers further include a surface that is inverted relative to the cylindrical surface to form barbs.

3. The fusion implant system as set forth in claim 2, wherein the implant has a longitudinal axis and the first end section terminates in a first end and the second end section terminates in a second end and the cylindrical surface of the second end section includes a external minor diameter section and the second end section has at least one external conical section that tapers from a larger external diameter to a smaller external diameter in the direction from the first end toward the second end, and has a surface that forms an angle with the external minor diameter section and the second end section includes at least two longitudinal slots in the cylindrical surface and the conical section placed about the longitudinal axis of the implant .

4. The fusion implant system as set forth in claim 3, wherein the second end section includes a plurality of external conical sections.

5. The fusion implant system as set forth in claim 4, wherein the longitudinal slots end at a distance X along the longitudinal axis from the end of the second end section and at least one of the external conical sections is placed at a greater distance than X from the end of the second end section.

6. An implant having a longitudinal axis and a first end section having an external thread and an integral second end section, the second section having a cylindrical base having at least one barb comprising a radially extending conical surface which has a larger diameter in the direction extending from the second end section to the first end section and the implant has a central cannulation along the longitudinal axis and wherein the cylindrical base of the second section includes at least two radial expansion slots which are placed radially symmetrically about the longitudinal axis of the second section whereby the at least one barb thereby has fingers which can flex radially inward to enable the second end section to be inserted into a pre-drilled hole and the cannulation in the second end section includes a restriction in the diameter of the cannulation whereby the barb flexes radially outward in response to a guide wire being driven through the restriction.

7. The implant as set forth in claim 6 wherein the first end section further includes a collar having flat surfaces for driving the thread into a section of bone.

8. The implant as set forth in claim 6 wherein the at least one barb is radially symmetrical.

9. The implant as set forth in claim 6 wherein the second end section forms an angle of 5° to 20° along the longitudinal axis from the first end section.

10. The implant as set forth in claim 6 wherein the cannulation has a length and a diameter which is constant through its length.

11. The implant as set forth in claim 6 wherein the barb is formed as a plurality of conical collars that include at least one split.

12. The implant as set forth in claim 11 wherein there are at least two longitudinally spaced conical collars.

13. The implant as set forth in claim 6 wherein the barb is formed as from one to not more than three longitudinally spaced conical collars.

* * * * *